US005922612A

United States Patent [19]

Alder et al.

[11] Patent Number: 5,922,612

[45] Date of Patent: Jul. 13, 1999

[54] OPTICAL SENSOR SYSTEM FOR DETERMINING PH VALUES AND IONIC STRENGTHS

[75] Inventors: Alex Alder, Arisdorf, Switzerland; Steven Barnard, Wellesley Hills, Mass.; Joseph Berger, Basel, Switzerland; Nils Blom, Riehen, Switzerland; Marizel Rouilly, Gipf-Oberfrick, Switzerland

[73] Assignee: Novartis Corporation, Summit, N.J.

[21] Appl. No.: 08/737,034

[22] PCT Filed: Apr. 27, 1995

[86] PCT No.: PCT/IB95/00302

§ 371 Date: Jan. 2, 1997

§ 102(e) Date: Jan. 2, 1997

[87] PCT Pub. No.: WO95/30148

PCT Pub. Date: Nov. 9, 1995

[30] Foreign Application Priority Data

May 2, 1994 [CH] Switzerland ............................ 1360/94

[51] Int. Cl.[6] ..................................................... G01N 31/16

[52] U.S. Cl. .......................... 436/163; 436/172; 526/248; 526/320

[58] Field of Search .................................... 526/248, 320; 436/163, 172

[56] References Cited

U.S. PATENT DOCUMENTS

| | | |
|---|---|---|
| 4,716,118 | 12/1987 | Wolfbeis et al. . |
| 5,273,716 | 12/1993 | Allen et al. . |

FOREIGN PATENT DOCUMENTS

| | | |
|---|---|---|
| 0623599 | 11/1994 | European Pat. Off. . |
| 623599 | 11/1994 | European Pat. Off. . |
| 1141147 | 1/1969 | United Kingdom . |
| 8805533 | 7/1988 | WIPO . |
| 9428786 | 12/1994 | WIPO . |

OTHER PUBLICATIONS

Jordan et al., "Physiological pH fiber–optic chemical sensor based on energy transfer", Analytical Chemistry, vol. 59, No.3, 1987, pp. 437–439.

Derwent Abstrract No. 74–70279V corresponding to Japanese Patent JP 49062589.

Elstov "Dihydroxynaphthofluoran and its Properties" Chem Abstract vol. 109, (1988).

Kamogawa "Fluorescent Polymers"Chem Abstract, vol. 81, (1974).

Hielbert Synthesis of Fluorescent Muramyl Dipeptide Congeners, Chem. Abs. vol. 109, (1988).

*Primary Examiner*—Bernard Lipman
*Assistant Examiner*—N. Sarofim
*Attorney, Agent, or Firm*—Stephen G. Kalinchak

[57] ABSTRACT

A method for the independent, reversible, optical determination of the pH value and the ionic strength of an aqueous sample with the aid of two different sensors in accordance with the fluorescence method, in which method two optical sensors, which are each composed of polymers of different structure but each contain the same fluorescent dye and which each consist of a coated material composed of a) a carrier material, to which there is applied b) at least one water-insoluble layer of a polymer comprising at least one hydrophilic monomer (A) from the group of substituted olefins, and c) a proton-sensitive fluorescent dye which is bonded directly or via a bridge group to the spine of polymer b) or which is incorporated in polymer b), are brought into contact with an aqueous test sample, irradiated with exciting light, the fluorescence is measured and the pH values and the ionic strengths are calculated from the measured fluorescence intensities with reference to calibration curves.

27 Claims, No Drawings

OPTICAL SENSOR SYSTEM FOR DETERMINING PH VALUES AND IONIC STRENGTHS

This application is filed under 35 U.S.C. 371, based on International Application No. PCT/IB95/00302, which was filed Apr. 27, 1995.

The invention relates to an optical method for determining the pH value and the ionic strength of an electrolyte solution, to optical sensors for carrying out the method, to polymers and to a polymerisable composition, and to fluorescent dyes.

It is known that the $pK_a$ value of an indicator changes with the ionic strength of a solution and that that change is dependent upon the level of charge on the indicator. It has therefore already been proposed in DE-A-3 430 935 to use in the determination of the pH value the difference between the measured values of two sensors $M_1$ and $M_2$ having different ionic strength dependencies, which is a complex function of the ionic strength J, after calibration with known standard solutions by computation using a process control computer.

The optical determination of the ionic strength at a given pH value in accordance with the fluorescence method using two optical sensors is described in DE-A-3 430 935. In that instance the fluorescent dye of the sensors, which is the same for each sensor, is immobilised via bridge groups directly on the surface of glass carriers, one sensor containing additional charges for achieving a high polarity and ionic strength dependency, and the other sensor being so modified that it is substantially non-polar, hydrophobic and independent of the ionic strength. A very considerable disadvantage of those sensors is that the fluorescent dye is directly exposed to external effects of the measuring solutions, and influences both of a physical nature (for example dissolution of the dye, deposits on the surface) and of a chemical nature (decomposition of the dye) rapidly render the sensors unusable. In addition, in the case of excitation in an evanescent field, interference between the evanescent measurement field and the fluorescence of the test sample cannot be completely avoided, which reduces the accuracy of measurement. The response time of those sensors is short, however, since the fluorescent dye bonded to the surface immediately comes into contact with the electrolyte solution. The sensitivity is regarded as adequate.

It is also known from WO 93/07483 to use as pH indicators carriers coated with hydrophilic polymers containing a polymer-bonded dye, optical measurements being based on the absorption method. Fluorescence detection is not mentioned.

It has now been found that the service life and usable life of sensors for determining ionic strength and pH value can be considerably increased, that the sensitivity is not reduced but is actually increased and that the response times are not reduced but are even slightly increased when measurements are carried out with sensors in which the fluorescent dye is embedded in a polymer membrane and the membrane layers of the two sensors used for measurement have different polymer compositions. Those different compositions bring about, for example, differences in the hydrophilicity, polarity and/or dielectric constant and therewith a different dependency on ionic strength, without it being necessary to make provision for high charges in at least one sensor. It has been shown, surprisingly, that it is not necessary to use charged sensors but that even measurement in a virtually uncharged environment is possible. The embedding of the indicator dye in the sensor membrane brings about effective protection against damage and interference from the measuring medium, so that the usable life is extended also. In addition, in sensors that measure in an evanescent field of the substrate, the membrane keeps the sample solution geometrically remote from the detection zone on the surface of the waveguide, which in contrast to the sensors described in DE-A-3 340 935 prevents interference with the fluorescence of the sample solution. The photostability is surprisingly high, which ensures a longer usable life. The response times and the conditioning times correspond, despite the embedding of the fluorophore, to the short time periods required for optical measuring systems, those parameters being substantially dependent upon the thickness of the membrane. The sensitivity and the resolution in the measuring range are even somewhat improved as a result of the pH displacement between the calibration curves. It has also surprisingly been found that the $pK_a$ values can be displaced into other pH ranges by the choice of polymer, so that a considerably larger pH measuring range is covered in using the same fluorophore.

The change in the environment of the fluorophore, for example the local dielectric constant, can be used for the purpose of adjusting the ionic strength dependency which may be influenced substantially by the selection and the nature of the polymer and the concentration of the fluorophore. Using the measuring method found, both the ionic strength and the pH value of a solution can be determined. The sensors can be used repeatedly, optionally after cleaning, for example in continuous determinations.

The invention relates to a method for the independent, reversible, optical determination of the pH value and the ionic strength of an aqueous sample with the aid of two different sensors in accordance with the fluorescence method, in which method two optical sensors, which are each composed of polymers of different structure but each contain the same fluorescent dye and which each consist of a coated material composed of a) a carrier material, to which there is applied b) at least one water-insoluble layer of a polymer comprising at least one hydrophilic monomer (A) from the group of substituted olefins, and c) a proton-sensitive fluorescent dye which is bonded directly or via a bridge group to the spine of polymer b) or which is incorporated in polymer b), are brought into contact with an aqueous test sample, irradiated with exciting light, the fluorescence is measured and the pH values and the ionic strengths are calculated from the measured fluorescence intensities with reference to calibration curves.

Hydrophilic may mean a solubility in water of at least 1 percent by weight, preferably at least 10 percent by weight, more preferably at least 20 percent by weight, most preferably at least 40 percent by weight, and particular preferred at least 50 percent by weight, whereby the percents by weight are related to the solution.

In detail, a procedure may be carried out in which, after calibration with samples of known ionic strength and known pH, the fluorescence intensity in contact with an electrolyte solution of unknown composition is measured and the contributions of the ionic strength and the pH to the measured fluorescence intensity are separated from one another by calculation. The measurement data obtained from the calibrations are evaluated by calculation, for example using a pattern recognition algorithm. Using the calculation method the pH and the ionic strength can then be determined from the measurement data obtained. Both pre-calibration and direct calibration can be carried out.

The sensors are brought into contact with the calibration solutions or with the test samples. This can be done by hand (for example using pipettes) or with a suitable automatic throughflow system, the sensors being rigidly mounted in a flow cell. Such throughflow cells are known to the person skilled in the art and they can be simply adapted to the particular intended use.

As light sources for exciting the fluorescence it is possible to use UV lamps (for example mercury vapor lamps, halogen lamps), lasers, diode lasers and light-emitting diodes. It may be advantageous to use filters to filter out light of the wavelength at which the fluorescent dye has an absorption maximum. The fluorescent light emitted by the sensors can be collected, for example using a lens system, and then guided to a detector, for example a secondary electron multiplier or a photodiode. The lens system can be so arranged that the fluorescence radiation through the transparent carrier, over the edges of the carrier or through the analysis sample is measured. Advantageously the radiation is guided in a manner known per se via a dichroic mirror. The fluorescence of the sensors is preferably measured while in contact with the calibration or sample solutions.

Sensors in which the fluorophore is incorporated in the polymer are generally suitable for once-only use. If the polymer membrane is provided with a permeable and hydrophilic protective layer it is possible both for those sensors and for sensors having polymer-bonded fluorophores generally (which may likewise have a protective layer on the membrane) to be used repeatedly or in continuous measurements.

The geometric shape of the carrier material may vary to a very great extent; for example, it may be in the form of fibers, cylinders, spheres, cuboids or cubes. Also possible are throughflow systems in which continuous measurements or successive measurements can be made. Planar sensors are preferred. The carrier material is preferably transparent. It may be, for example, inorganic glass or transparent plastics, such as polycarbonate, polyesters, polyamides or polyacrylates or polymethacrylates. In another preferred form the carrier material of the optical sensors is transparent and preferably consists of glass or a transparent polymer.

The planar sensor may have any desired external shape, for example it may be square, rectangular or round. It may have a surface area of from 0.01 to approximately 50 $cm^2$, advantageously from 0.02 to 10 $cm^2$. The measuring region of the sensor may have an area of, for example, less than 5 $mm^2$, preferably less than or equal to 2 $mm^2$. The measuring region can be identical to a fully coated surface of the sensor. Advantageously a coating provided on both sides but locally separated can be used.

The polymers in layer b) preferably comprise at least 50 mol % monomer (A), based on the polymer.

The hydrophilic monomer (A) is preferably an olefinic monomer which may correspond to formula XX $$Z_x—CR=CR_2 \qquad (XX)$$

wherein each R independently of the others is hydrogen or a hydrophobic substituent, and $Z_x$ is a hydrophilic radical.

The hydrophobic substituents may be, for example, $C_1$–$C_{12}$alkyl, $C_1$–$C_{12}$alkoxy, $C_1$–$C_{12}$haloalkyl, phenyl, halophenyl, $C_1$–$C_4$alkylphenyl, $C_1$–$C_4$alkoxyphenyl, carboxylic acid ester groups having a total of from 2 to 20 carbon atoms, —CN, F or Cl.

The hydrophilic radicals may be, for example, —OH, —O—($C_2$–$C_{12}$alkylene)—OH, —C(O)—$NH_2$, —C(O)—NH—($C_2$–$C_{12}$alkylene)—OH, —C(O)—N—($C_2$–$C_{12}$alkylene)$_2$—OH, —C(O)—NH—$C_1$–$C_{12}$alkyl, —C(O)—N—($C_1$–$C_{12}$alkyl)$_2$, pyrrolidonyl or —C(O)—O—($C_2$–$C_{12}$alkylene)—OH.

The thickness of polymer layer b) may be, for example, from 0.01 to 50 μm, preferably from 0.1 to 25 μm and especially from 0.1 to 10 μm.

Being composed of different polymers means that the different dependencies of the sensors on the ionic strength is determined by the polymer composition and the properties of the membrane. Structural differences can be achieved, for example, by a different content of fluorophores, the incorporation or immobilisation thereof in or on the polymer, different amounts of monomers, different monomers involved in the polymer structure and/or different cross-linking agents and/or different polymers in admixture with polymerisable monomers. One of the sensors must always exhibit an ionic strength dependency, while the other sensor has no ionic strength dependency or a different ionic strength dependency.

The sensors are therefore coated with different polymer membranes so that they have different dependencies on the ionic strength. For the method according to the invention it is best to select polymers in which there is a large difference in the ionic strength dependency. Advantageously the difference in ionic strength dependency is at least 0.1, preferably at least 0.15 and especially at least 0.2, measured as the $pK_a$ displacement between the calibration curves in buffer solutions of 0.1M and 0.3M ionic strength. An advantageous practical range of ionic strength difference is from 0.1 to 0.15.

Combinations of polymers based on polyvinylpyrrolidone with polymers based on polyhydroxyethylmethacrylic acid or based on polyacrylamides have proved advantageous, for example, in measurements in the physiological range (for example the determination of the pH value of blood or serum).

The sensor may have one or more locally separated membrane layers; in the latter case, parallel measurements with the same or different test samples can be carried out.

The polymers of layer b) may be cross-linked, for example with from 0.01 to 50 mol %, preferably from 0.1 to 20 mol % and especially from 0.5 to 10 mol %, of a cross-linking agent, based on the polymer. Suitable cross-linking agents are, for example, acrylic or methacrylic acid esters or amides of polyols, preferably diols to tetrols, or polyamines, preferably diamines to tetramines. Such cross-linking agents are known and many are described in the literature. Some examples of polyols are ethylene glycol, 1,3-propanediol, 1,4-butanediol, 1,6-hexanediol, diethylene glycol, 1,1,1-trihydroxymethyl-ethane or -propane, pentaerythritol and dipentaerythritol. Some examples of polyamines are ethylenediamine, 1,3-propanediamine, 1,4-butanediamine, 1,6-hexanediamine, diethylenetriamine and triethylenetetramine. Another known cross-linking agent is, for example, divinylbenzene. Other suitable crosslinking agents are alkylene-bis-dialkylmaleinimidyle compounds like ethylene bis-(dimethyl)maleinimidyle.

Polymers b) may be composed partly or completely of at least one hydrophilic monomer (A) and, optionally, hydrophobic monomer. The polymers b) preferably comprise at least 20 mol %, more preferably at least 30 mol %, especially at least 40 mol %, more especially at least 50 mol %, preferably at least 80 mol % of monomer (A), and accordingly at most 80 mol %, more preferably at most 70 mol %, especially at most 60 mol %, more especially at most 50 mol %, and preferably at most 20 mol %, of a hydrophobic comonomer (B), based on the polymer.

Polymer b) may comprise, for example, from 20 to 100 mol %, preferably from 20 to 80 mol %, of at least one structural unit of formula III (III)

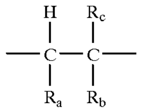

and from 80 to 0 mol %, preferably from 80 to 20 mol %, of at least one structural unit of formula IV (IV)

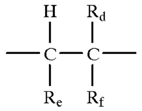

wherein $R_a$ is hydrogen, $C_1$–$C_6$alkyl or —$COOR_g$ and $R_g$ is hydrogen, $C_1$–$C_6$alkyl, $C_1$–$C_6$hydroxyalkyl or an alkali metal cation, for example $Na^{\oplus}$ or $K^{\oplus}$, $R_b$ is pyrrolidonyl, —OH, $C_2$–$C_6$hydroxyalkoxy, —$CONR_7R_8$ or —$COOR_9$, $R_7$ and $R_8$ are each independently of the other hydrogen, $C_1$–$C_6$alkyl or $C_2$–$C_6$hydroxyalkyl and $R_9$ is hydrogen or $C_1$–$C_6$hydroxyalkyl, $R_c$ is hydrogen or $C_1$–$C_6$alkyl, $R_d$ is hydrogen, $C_1$–$C_6$alkyl, F or Cl, $R_e$ is hydrogen or $C_1$–$C_6$alkyl, or $R_e$ and $R_f$ together are —CO—O—CO—, and $R_f$ is hydrogen, $C_1$–$C_6$alkyl, —CN, F or Cl.

In a preferred form, the layer is composed of polymers having 100 mol % of structural units of formula III, with especially $R_a$ being hydrogen, $R_c$ being hydrogen or methyl and $R_b$ being pyrrolidonyl, —$CONR_7R_8$ or —$COOR_9$, $R_7$ and $R_8$ each independently of the other being hydrogen, $C_1$–$C_6$alkyl or $C_2$–$C_6$hydroxyalkyl and $R_9$ being hydrogen or $C_2$–$C_6$hydroxyalkyl.

In a preferred sub-group, the polymer layer is formed by polymers comprising from 20 to 80 mol % of at least one structural unit of formula IIIa (IIIa)

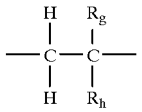

and from 80 to 20 mol % of at least one structural unit of formula IIIb (IIIb)

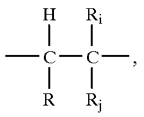

wherein $R_g$ and $R_i$ are each independently of the other hydrogen or methyl, preferably hydrogen;

$R_h$ is di($C_1$–$C_6$alkyl)amino, preferably di($C_1$–$C_4$alkyl) amino, and especially dimethylamino or diethylamino; and $R_j$ is amino, preferably mono($C_1$–$C_6$alkyl)amino and especially mono($C_1$–$C_6$alkyl)amino, for example tert-butylamino. Such polymer membranes (with the exception of those wherein $R_j$=amino) are suitable especially for pH measurements in the physiological range around about 7.4. Despite being very hydrophobic they still have adequate response times, but they are not water-soluble and therefore do not need to be cross-linked, and they can be prepared from solutions of the corresponding monomers, for example by means of spin casting.

The water-insoluble layer having hydrophilic monomers (A) may be, for example, especially a layer obtainable by the following process: polymerisation in solution of at least one hydrophilic monomer (A) from the group of substituted olefins in the presence of a carrier polymer comprising at least one hydrophilic monomer (A) from the group of substituted olefins that is identical to or different from the former. Those polymers are preferably cross-linked, for example with diolefinic cross-linking agents. The amount of crosslinking agent may be from 0.1 to 30% by weight, preferably from 0.5 to 20% by weight and especially from 1 to 10% by weight, based on monomer (A) and the carrier polymer. Polymerisates so prepared form polymer networks in which the carrier polymer is embedded. Such polymer membranes are distinguished by good mechanical properties and high durability, which ensure a long usable life. A special advantage is their ease of manufacture and the control of the layer thickness by means of spin casting processes, since the viscosity of the casting solutions can be set in a targeted manner by way of the content and the choice of carrier polymer. The carrier polymer is preferably hydrophilic. A further advantage is the polymerisation and/or cross-linking directly on the carrier by the action of heat and/or actinic radiation.

Suitable carrier polymers are, for example, those having an average molecular weight of from 10 000 to 500 000 daltons, preferably from 20 000 to 350 000 daltons, determined by the gel permeation method using standard polymers of known molecular weight.

Suitable mixture ratios between monomer (A) and carrier polymer are, for example, from 5 to 95% by weight, preferably from 30 to 70% by weight, of carrier polymer, and from 95 to 5% by weight, preferably from 70 to 30% by weight, of monomer A, based on the total mixture of monomer and carrier polymer.

The hydrophilic carrier polymers may be selected, for example, from the group of homo- and co-polymers of vinylpyrrolidone; of hydroxyalkyl acrylates and methacrylates; of vinyl alcohol; of vinylhydroxyalkyl ethers; of acrylamides and methacrylarnides; or of hydroxyalkyl acrylamides and methacrylamides. Such polymers are known and are to some extent commercially available or can be prepared in accordance with analogous processes. The hydroxyalkyl groups may contain from 2 to 12, preferably from 2 to 6, carbon atoms. The desired degree of hydrophilicity can be adjusted using hydrophobic olefinic comonomers. The N atoms of acrylamides and methacrylamides can be mono- or di-substituted by $C_1$–$C_6$alkyl. In an advantageous form the carrier polymer is composed of monomer (A), and monomer (A) is simultaneously used together with that carrier polymer for the preparation of the membrane.

Some examples of hydrophilic carrier polymers are polyvinylpyrrolidone, poly($C_2$–$C_6$hydroxyalkyl) acrylates and methacrylates, for example polyhydroxyethyl methacrylate, polyhydroxypropyl methacrylate, polyhydroxybutyl methacrylate, polyhydroxyhexyl methacrylate, polyhydroxyethyl acrylate, polyhydroxypropyl acrylate, polyhydroxybutyl acrylate or polyhydroxyhexyl acrylate, polyacrylamide or polymethacrylamide, mono($C_1$–$C_6$alkyl) polyacrylamide or mono($C_1$–$C_6$alkyl)polymethacrylamide, di($C_1$–$C_6$alkyl)polyacrylamide or di($C_1$–$C_6$alkyl) polymethacrylamide.

In an especially preferred form the polymer layer comprises at least one monomer (A) from the group: vinylpyrrolidone, 2-hydroxyethyl methacrylate, 3-hydroxypropyl methacrylate, 4-hydroxybutyl acrylate, 5-hydroxypentyl acrylate, 6-hydroxyhexyl acrylate, acrylamide, N,N-dimethylacrylamide and tert-butylacrylamide, or a polymer obtainable by polymerisation in solution of a monomer (A) from the group: vinylpyrrolidone, 2-hydroxyethyl methacrylate, 3-hydroxypropyl methacrylate, 4-hydroxybutyl acrylate, 5-hydroxypentyl acrylate, 6-hydroxyhexyl acrylate and acrylamide, in the presence of a carrier polymer of a monomer (A) from the group consisting of vinylpyrrolidone, 2-hydroxyethyl methacrylate, 3-hydroxypropyl methacrylate, 4-hydroxybutyl acrylate and acrylamide.

The fluorescent dye may be present, for example, in an amount of from 0.01 to 10% by weight, preferably from 0.1 to 5% by weight and especially from 0.5 to 3% by weight, based on the polymer. The fluorescent dye is preferably covalently bonded to the polymer spine via a bridge group.

Suitable proton-sensitive fluorescent dyes are, for example, those of the group of xanthenes and benzoxanthenes (for example fluorescein, halogenated fluoresceins, seminaphthofluoresceins, seminaphthorhodafluores, 2,3-benzfluorescein, 3,4-benzfluorescein, the isomers of benzrhodamine and substituted derivatives, the isomers of benzchromogene and substituted derivatives); acridines (for example acridine, 9-amino-6-chloroacridine); acridones (for example 7-hydroxyacridone, 7-hydroxybenzacridone); pyrenes (for example 8-hydroxypyrene-1,3,6-trisulfonic acid); cyanine dyestuffs; and coumarins (for example 7-hydroxycoumarin, 4-chloromethyl-7-hydroxycoumarin). The fluorescent dyes can be functionalised for bonding to a polymer backbone.

Suitable bridge groups for bonding the fluorescent dye to the polymer spine are, for example, —O—C(O)—, —C(O)—O—$C_2$-$C_{12}$alkylene-O—C(O)—, —NH—C(O)—O— and —NH—C(O)—O—$C_2$-$C_{12}$alkylene-O—C(O)—, —C(O)—O—($C_2$-$C_6$alkylene-O)$_{1\ bis\ 12}$—, —C(O)—O—($C_2$-$C_6$alkylene-O)$_{1\ bis\ 12}$—$C_2$-$C_6$alkylene-NH—, —C(O)—NH—($C_2$-$C_6$alkylene-O)$_{1\ bis\ 12}$—$C_2$-$C_6$alkylene-NH—, —C(O)—NH—(($C_2$-$C_6$alkylene-O)$_{1\ bis\ 12}$—$CH_2$—C(O)—NH—. The alkylene in the repeating alkylene-O— residues may be for example ethylene or 1,2-propylene.

The bridge group of the fluorescent dye is preferably a group —$(CO)_s$—NH—($C_2$-$C_{12}$alkylene-O)$_r$—CO— or —$(CO)_s$—O—($C_2$-$C_{12}$alkylene-O)$_r$—CO— or —C(O)—NH—($CH_2CH_2$—O)$_{1\ bis\ 6}$—$CH_2$C(O)—NH—, with the $(CO)_s$ group or the NH group being bonded to the fluorescent dye and r and s each being 0 or 1. The alkylene preferably contains from 2 to 6 carbon atoms and is especially ethylene.

The fluorescent dye bonded to the spine of the polymer may be, for example, a dye of formula I, II or IIa (I)

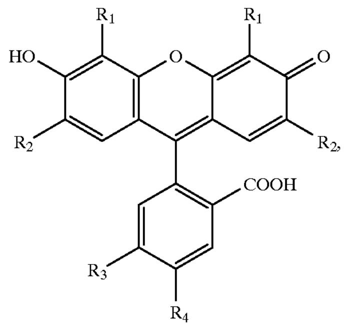

(II)

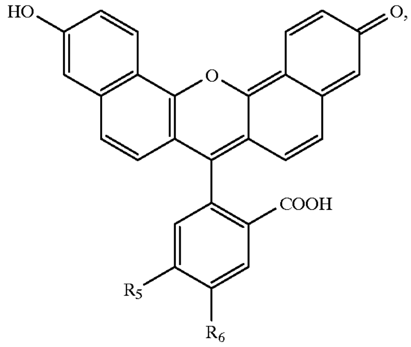

(IIa)

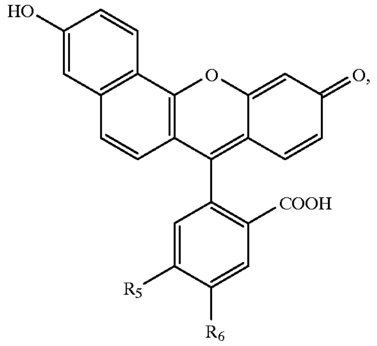

wherein $R_1$ and $R_2$ are each independently of the other hydrogen, $C_1$-$C_4$alkyl, $C_1$-$C_4$alkoxy, $C_1$-$C_4$alkoxycarbonyl, $C_1$-$C_4$alkyl-$SO_2$— or halogen, and either $R_3$ is hydrogen and $R_4$ is —NH—CO—, —CO—NH—($C_2$-$C_{12}$alkylene-O)—CO—, —CO—NH—($C_2$-$C_{12}$alkylene-NH)—CO— or —C(O)—NH—($CH_2CH_2$—O)$_{1\ bis\ 6}$—$CH_2$C(O)—NH—, or $R_3$ is —NH—CO—, —CO—NH—($C_2$-$C_{12}$alkylene-O)—CO—, —CO—NH—($C_2$-$C_{12}$alkylene-NH)—CO— or —C(O)—NH—($CH_2CH_2$—O)$_{1\ bis\ 6}$—$CH_2$C(O)—NH— and $R_4$ is hydrogen; or wherein either $R_5$ is hydrogen and $R_6$ is —NH—C(O)—, —CO—NH—($C_2$-$C_{12}$alkylene-O)—CO—, —CO—NH—($C_2$-$C_{12}$alkylene-NH)—CO— or —C(O)—NH—($CH_2CH_2$—O)$_{1\ bis\ 6}$—$CH_2$C(O)—NH—, or $R_5$ is —NH—C(O)—, —CO—NH—($C_2$-$C_{12}$alkylene-O)—CO—, —CO—NH—($C_2$-$C_{12}$alkylene-NH)—CO— or —C(O)—NH—($CH_2CH_2$—O)$_{1\ bis\ 6}$—$CH_2$C(O)—NH—, and $R_6$ is hydrogen, in each case in free form or in salt form, and the $C_1$-$C_{20}$alkyl esters thereof.

The compounds of formulae I, II and especially IIa are distinguished by an excitation absorption in the visible range, by longer-wavelength fluorescence and by excellent photostability, so that commercially available radiation sources can be used for the fluorescence excitation, which meets the excitation wave-lengths.

It has also been found, surprisingly, that the $pK_a$ value of the fluorophore can be systematically varied and matched to the desired pH measuring range if the hydrophilicity of polymers composed only of acrylamides or methacrylamides and N-substituted acrylamides or methacrylamides or only of at least two different N-substituted acrylamides or methacrylamides is set by their composition and the fluorophore is covalently bonded to the polymer. It has also been found that the viscosity of coating compositions comprising such polymers can be so adjusted that technically advantageous and economic coating methods, such as, for example, spin casting, can be used.

The invention therefore relates also to a copolymer comprising at least one recurring structural unit of formula VII (VII)

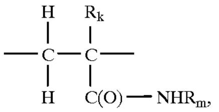

optionally at least one recurring structural unit of formula VIII (VIII)

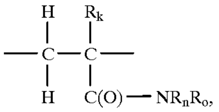

and recurring structural units of formula IX (IX)

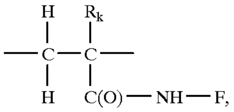

wherein $R_k$ is hydrogen or methyl, $R_m$ is hydrogen or $C_1$–$C_{12}$alkyl, phenyl or benzyl, $R_n$ and $R_o$ are each independently of the other $C_1$–$C_{12}$alkyl, phenyl or benzyl or $R_n$ and $R_o$ together are tetramethylene, pentamethylene, —$(CH_2)_2$—O—$(CH_2)_2$— or —$(CH_2)_2$—N($C_1$–$C_6$alkyl)—$(CH_2)_2$—, and F is the radical of a fluorophore bonded directly or via a bridge group to the N atom, with the proviso that at least two different recurring structural units of formula VII or at least one structural unit of formula VII and at least one structural unit of formula VIII are present.

$R_m$, $R_n$ and $R_o$ as alkyl contain preferably from 1 to 6 carbon atoms. Preferred copolymers are those having structural units of formula VII and structural units of formula VIII, with $R_m$ being preferably $C_1$–$C_{12}$alkyl, more preferably $C_1$–$C_6$alkyl.

The structural units of formula VII may be present in an amount of from 10 to 80 mol %, preferably from 20 to 70 mol %, and the structural units of formula VIII in an amount of from 90 to 20 mol %, preferably from 80 to 30 mol %, based on the polymer. The polymer can additionally be cross-linked, especially when possible water-solubility or too high a water-solubility is to be prevented. Suitable cross-linking agents have been mentioned above. The bivalent structural units of the cross-linking agent may be present, for example, in an amount of from 0.1 to 30% by weight, preferably from 0.5 to 20% by weight and especially from 1 to 10% by weight, based on the polymer. The fluorophore radical F can be derived from the fluorophores mentioned above and is especially a fluorophore of formula I, II or IIa. The structural unit of formula IX may be present in an amount of from 0.1 to 10 mol %, preferably from 0.5 to 5 mol %, based on the polymer.

In an especially preferred form the polymer comprises structural units of formula VII and structural units of formula VIII, $R_k$ is hydrogen, $R_m$ is $C_3$–$C_6$alkyl, $R_n$ and $R_o$ are $C_1$- or $C_2$-alkyl and F is a radical of formula I, II or IIa.

The invention relates also to a polymerisable composition comprising a) an acrylamide or methacrylamide of formula X (X)

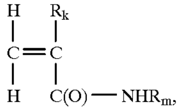

b) optionally an acrylamide or methacrylamide of formula XI (XI)

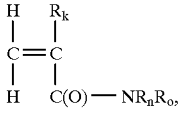

c) an acrylamide or methacrylamide of formula XII (XII)

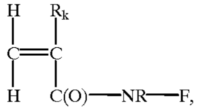

and d) optionally an at least diolefinic cross-linking agent, wherein $R_k$, $R_m$, $R_n$ and $R_o$ and also F are as defined above, with the proviso that at least two different monomers of formula X or at least one structural unit of formula XI and at least one structural unit of formula X are present.

The composition is subject to the same preferences and has the same forms as given above for the corresponding polymers. The compositions may comprise further additives, for example solvents, thermal polymerisation initiators, such as, for example, radical formers, photoinitiators for the photopolymerisation, processing auxiliaries and stabilisers, such as, for example, anti-oxidants and/or light-protecting agents.

The invention relates also to a sensor comprising a material coated with a water-insoluble and hydrophilic polymer, the polymer containing an indicator dye, wherein a) there is applied to a carrier material b) a water-insoluble layer of a polymer comprising at least one hydrophilic monomer (A) from the group of substituted olefins, and c) a proton-sensitive fluorescent dye is covalently bonded directly or via a bridge group to the spine of the polymer b) or is incorporated in polymer b).

"Incorporated" means the presence of a preferably homogeneous mixture.

The forms and preferences indicated above apply to the sensors. In an advantageous form an adhesion-promoting layer is arranged between the carrier material and the polymer layer. The polymer layer can be provided with a proton-permeable protective layer.

The sensors are suitable also for pH measurement at physiological temperatures and they are especially suitable for measurements in the physiological pH range of approximately from 6 to 8 and especially from 6.4 to 7.6. The response times may be under 30 seconds and a first measurement is possible after less than about 5 minutes. The sensors are also distinguished by a high degree of storage stability.

The sensors can be prepared in accordance with coating techniques known per se. In order to improve adhesion the carrier materials can be treated beforehand with adhesion promoters. For the same purpose, it is also possible to carry out plasma treatment of the carrier material in order to generate functional groups on the surface. The surface can also be provided with copolymerisable groups in order to achieve an especially high degree of adhesion. Known adhesion promoters for glass are, for example, triethoxyglycidyloxysilane, 3-azidopropyl-triethoxysilane or 3-aminopropyl-triethoxysilane. The surfaces so treated can be further modified, for example with O-(N-succinimidyl)-6-(4'-azido-2'-nitrophenylamino)-hexanoate. It has proved especially advantageous to treat the surfaces with silanes of ethylenically unsaturated carboxylic acid esters, such as, for example, methacrylic acid 3-trimethoxysilylpropyl ester, because in the polymerisation the layer can be anchored covalently to the surface. Known coating techniques are, for example, spreading, immersion, knife application, spraying, casting, curtain casting or spin casting.

For coating it is possible to use either solutions of polymerisates according to the invention, or hydrophilic monomers (A) optionally mixed with a hydrophilic carrier polymer and/or a cross-linking agent, that contain a copolymerisable fluorescent dye, in the second case the polymerisation being carried out after coating. The polymerisation can be initiated thermally, for example with initiators such as α,α'-azobisisobutyronitrile or ammonium peroxodisulfate, or by the action of radiation, such as, for example, UV light with the concomitant use of photoinitiators and optionally sensitisers. Examples of photo-initiators are benzophenones, xanthones, thioxanthones and α-sec-amino-acetophenones.

Copolymerisable fluorescent dyes contain, for example, an ethylenically unsaturated group (vinyl, crotonyl, methallyl) that is bonded directly or via a bridge group to the fluorescent dye. The monomers (A) and the carrier polymers are known. A known copolymerisable fluorescent dye is, for example, 3- or 4-acryloylaminofluorescein.

Polymers containing fluorescent dyes having the bridge groups —O—C(O)— and —C(O)—O—$C_2$–$C_{12}$alkylene-O—C(O)— are obtainable, for example, by esterification with fluorescent dyes that contain carboxy or hydroxy groups. Polymers containing fluorescent dyes having the bridge groups —NH—C(O)—O— and —NH—C(O)—O—$C_2$–$C_{12}$alkylene-O—C(O)— are obtainable, for example, via isocyanate-functionalised fluorescent dyes and hydroxy-group-containing polymers.

The reactions described above can be carried out in a manner known per se, for example in the absence or presence of a suitable solvent, the reactions being carried out, as necessary, with cooling, at room temperature or with heating, for example in a temperature range of from approximately 5° C. to approximately 200° C., preferably approximately from 20° C. to 120° C., and, if necessary, in a closed vessel, under pressure, in an inert gas atmosphere and/or under anhydrous conditions.

The starting materials mentioned hereinabove and hereinbelow that are used for the preparation of the polymers are known or can be prepared in accordance with methods known per se.

The reactants can be reacted with one another as such, that is to say without the addition of a solvent or diluent, for example in the molten state. It is generally advantageous, however, to add a solvent or diluent or a mixture of solvents. Examples of such solvents and diluents that may be mentioned are: water; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide.

By the choice of the monomers and polymers to be used according to the invention it is possible in a targeted manner to vary the properties of the sensor membranes, such as, for example, hydrophilicity, degree of swelling or polarity, within a wide range. As a result, it is possible to prepare using the same indicator dye sensor membranes that can be optimised for various pH ranges and that react differently to the ionic strength of the solution (see also Tables 4 and 5). In addition, the method of preparing the sensor membrane allows industrially applicable processes (for example rotation coating) to be used for the coating of planar carrier materials of glass or plastics for the economic mass production of planar sensors.

The invention relates also to compounds of formulae Ia, IIc and IId (Ia)

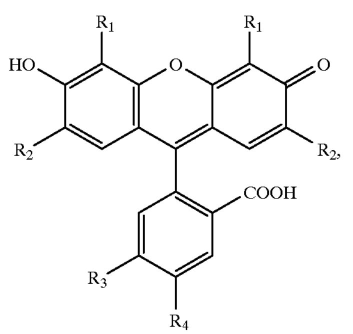

-continued (IIc)

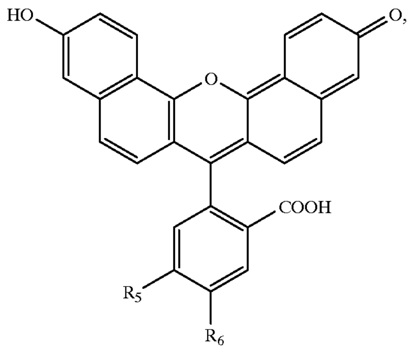

(IId)

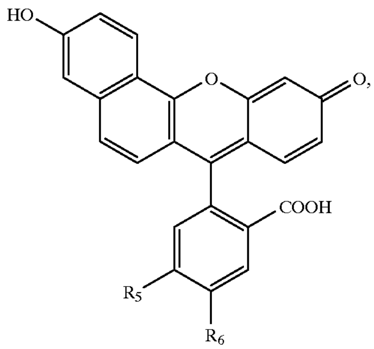

wherein $R_1$ and $R_2$ are each independently of the other hydrogen, $C_1$–$C_4$alkyl, $C_1$–$C_4$alkoxy, $C_1$–$C_4$alkoxycarbonyl, $C_1$–$C_4$alkyl-$SO_2$— or halogen, and either $R_3$ or $R_5$ is hydrogen and $R_4$ or $R_6$ is a group —$(CO)_s$—O—($C_2$–$C_{12}$alkylene-O$)_r$—CO—$CR_k$=$CH_2$, —$(CO)_s$—NH—($C_2$–$C_{12}$alkylene-NH$)_r$—CO—$CR_k$=$CH_2$, —NH—C(O)—($C_2$–$C_{12}$alkylene-NH$)_r$—CO—$CR_k$=$CH_2$, —$(CO)_s$—O—($C_2$–$C_{12}$alkylene-O$)_r$—CO—$CR_k$=$CH_2$, —$(CO)_s$—O—($C_2$–$C_{12}$alkylene-O$)_r$—$C_2$–$C_6$-alkylene-NH—CO—$CR_k$=$CH_2$, —NH—($C_2$–$C_{12}$alkylene-O$)_r$—$C_2$–$C_6$-alkylene-NH—CO—$CR_k$=$CH_2$, or —NH—C(O)—$CH_2$—O—($C_2$–$C_{12}$alkylene-O$)_r$—$C_2$–$C_6$-alkylene-NH—CO—$CR_k$=$CH_2$, or $R_3$ or $R_5$ is a group —$(CO)_s$—NH—($C_2$–$C_{12}$alkylene-O$)_r$—CO—$CR_k$=$CH_2$, —$(CO)_s$—NH—($C_2$–$C_{12}$alkylene-NH$)_r$—CO—$CR_k$=$CH_2$, —NH—C(O)—($C_2$–$C_{12}$alkylene-NH$)_r$—CO—$CR_k$=$CH_2$, or —$(CO)_s$—O—($C_2$–$C_{12}$alkylene-O$)_r$—CO—$CR_k$=$CH_2$, —$(CO)_s$—O—($C_2$–$C_{12}$alkylene-O$)_r$—$C_2$–$C_6$-alkylene-NH—CO—$CR_k$=$CH_2$, —NH—($C_2$–$C_{12}$alkylene-O$)_r$—$C_2$–$C_6$-alkylene-NH—CO—$CR_k$=$CH_2$, or —NH—C(O)—$CH_2$—O—($C_2$–$C_{12}$alkylene-O$)_r$—$C_2$–$C_6$-alkylene-NH—CO—$CR_k$=$CH_2$, and $R_4$ and $R_6$ are hydrogen, r and s are each 0 or 1, and $R_k$ is methyl or hydrogen; with the proviso that $R_1$ and $R_2$ are other than hydrogen when $R_3$ or $R_4$ is acryloylamino; in each case in free form or in salt form, and the $C_1$–$C_{20}$alkyl esters thereof.

The alkylene in the alkylene-O— residue preferably contains from 2 to 6 carbon atoms, is preferably linear and is especially ethylene. In the case of $R_3$ and $R_4$, in the group —$(CO)_s$—NH—($C_2$–$C_{12}$alkylene-O$)_r$—CO—$CR_h$=$CH_2$ preferably s and preferably also r is 0. In the case of $R_5$ and $R_6$, in the group —$(CO)_s$—NH—($C_2$–$C_{12}$alkylene-O$)_r$—CO—$CR_h$=$CH_2$ preferably s and preferably also r is 1.

Unless defined to the contrary, the general terms used hereinbefore and hereinbelow have the following preferred meanings:

Halogen is fluorine, chlorine, bromine or iodine, especially fluorine, chlorine or bromine, more especially chlorine or bromine.

Unless defined to the contrary, carbon-containing groups or structural units each contain from 1 up to and including 4, preferably 1 or 2, carbon atoms.

Alkyl—as a group per se and as a structural unit of other groups, such as alkoxy and alkoxycarbonyl—is, giving due consideration to the number of carbon atoms present in the group or compound in question, either straight-chain, that is to say methyl, ethyl, propyl or butyl, or branched, for example isopropyl, isobutyl, sec-butyl or tert-butyl.

Examples of $R_3$ or $R_4$ and $R_5$ or $R_6$ are the acryloylamine group —NHCOCH=$CH_2$, the methacryloylamine group —NHCOC($CH_3$)=$CH_2$ and the 2-(methacryloyloxy)-ethylaminocarbonyl group —CONH$CH_2CH_2$OCOC($CH_3$)=$CH_2$.

Preferred forms within the scope of the invention, taking into consideration the proviso mentioned above, are:

(1) A compound of formula Ia wherein $R_1$ is hydrogen, $C_1$–$C_2$alkyl, $C_1$–$C_2$alkoxy, $C_1$–$C_2$alkoxycarbonyl or halogen, preferably hydrogen or $C_1$–$C_2$alkyl, especially hydrogen or methyl.

(2) A compound of formula Ia wherein $R_2$ is hydrogen, $C_1$–$C_2$alkyl, $C_1$–$C_2$alkoxy, $C_1$–$C_2$alkoxycarbonyl or halogen, preferably hydrogen or $C_1$–$C_2$alkyl, especially hydrogen or methyl, more especially hydrogen.

(3) A compound of formula Ia wherein either $R_3$ is hydrogen and $R_4$ is acryloylamino or methacryloylamino, especially acryloylamino, or $R_3$ is acryloylamino or methacryloylamino, especially acryloylamino, and $R_4$ is hydrogen.

Special preference within the scope of the invention is given to 4-acryloylamino-4',5'-dimethylfluorescein and 5-acryloylamino-4',5'-dimethylfluorescein as compounds of formula I. Very special preference within the scope of the invention is given to 4-acryloylaminofluorescein.

The compounds according to the invention can be prepared in accordance with processes known per se or analogous processes, for example by reacting a compounds of formula V, VI or VIa (V)

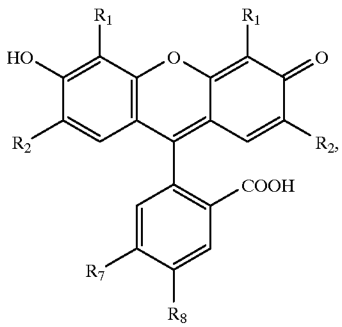

-continued (VI)

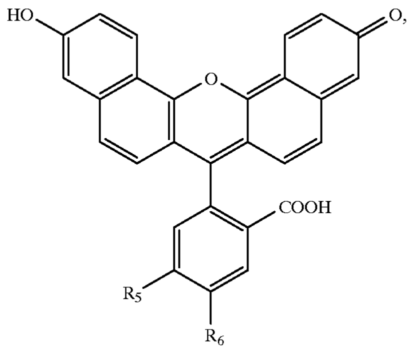

(VIa)

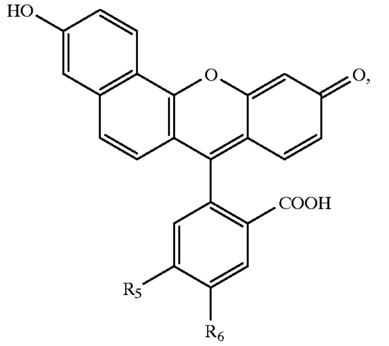

which are known or can be prepared analogously to known compounds, and wherein $R_1$ and $R_2$ are as defined for formulae Ia, II and IIa and $R_7$ is hydrogen and $R_8$ is —$NH_2$ or —$(CO)_s$—NH—$C_2$–$C_{12}$alkylene-OH or —$(CO)_s$—O—$C_2$–$C_{12}$alkylene-OH or $R_7$ is $NH_2$ or —$(CO)_s$—NH—$C_2$–$C_{12}$alkylene-OH or —$(CO)_s$—O—$C_2$–$C_{12}$alkylene-OH and $R_8$ is hydrogen, in free form or in salt form, optionally in the presence of a base, with an acrylic or methacrylic acid derivative of the formula $CH_2$=C($R_h$)COX wherein $R_h$ is hydrogen or methyl and X is a leaving group, for example halogen, especially chlorine.

Another possibility to manufacture compounds of formulae Ia, IIc and IId is the reaction of $CH_2$=C($R_h$)CO—$W_1$—C(O)X with compounds of the formulae V, VI or VIa, wherein either $R_7$ and $R_5$ or $R_8$ and $R_5$ are —OH or —$NH_2$, whereby $W_1$ means one of the linking groups defined for $R_3$ to $R_6$ in formulae Ia, IIc and IId.

The reaction can be carried out in a manner known per se, for example in the presence of a suitable solvent or diluent or a mixture thereof, the reaction being carried out, as necessary, with cooling, at room temperature or with heating, for example in a temperature range of from approximately −10° C. to the boiling temperature of the reaction medium, preferably from approximately 0° C. to approximately 25° C., and, if necessary, in a closed vessel, under pressure, in an inert gas atmosphere and/or under anhydrous conditions. Especially advantageous reaction conditions can be found in the Examples.

The starting materials used for the preparation of the compounds, in each case in free form or in salt form, are known or can be prepared in accordance with methods known per se.

The reactants can be reacted with one another as such, that is to say without the addition of a solvent or diluent, for example in the molten state. It is generally advantageous, however, to add an inert solvent or diluent or a mixture of at least two solvents. Examples of such solvents and diluents that may be mentioned are: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, it is also possible for bases, such as triethylamine, pyridine, N-methylmorpholine or N,N-diethylaniline, used in excess to act as solvent or diluent.

The reaction is advantageously carried out in a temperature range of from approximately −10° C. to approximately +40° C., preferably from 0° C. to approximately +20° C.

In a preferred form, a compound of formula V is reacted at from −10 to +40°, preferably 0°, in a ketone, preferably acetone, with acryloyl chloride.

The invention relates also to the use of two sensors according to the invention having different polymer compositions in layer b) in the optical determination of the ionic strength and the pH value of an electrolyte solution by means of fluorescence detection.

The following Examples serve to illustrate the invention. Temperatures are given in degrees Celsius.

A) Preparation of polymerisable fluorescent dyes

EXAMPLE A1

4-Acryloylaminofluorescein 1.26 ml of freshly distilled acryloyl chloride that have been dissolved in 1.5 ml of acetone are added dropwise at 0°, with stirring, to a solution of 5 g of 4-aminofluorescein in 150 ml of acetone. After one hour the crystalline product that has formed is filtered off with suction and washed twice each with acetone and ether. The product is then dried overnight under a high vacuum at room temperature. The dye decomposes from 200°.

$^1$H-NMR (DMSO-$d_6$): 10.9 (s,1H); 8.47 (d,1H); 7.96 (d×d,1H); 7.25 (d,1H); 6.25–6.75 (m,6H); 6.35 (d×d,1H); 5.85 (d×d,1H); IR (KBr): 2100–3650s (broad), 1705m, 1690m, 1675m, 1630s, 1600s $cm^{-1}$; MS: $M^+$=402; absorption spectrum (EtOH): $\lambda_{max}$=442 nm, e=9 970; (EtOH+2% 0.1N NaOH): $\lambda_{max}$=500 nm, ε=89 100. DMSO-$d_6$= deuterated dimethyl sulfoxide; EtOH=ethanol.

EXAMPLE A2

5-Acryloylaminofluorescein 180 mg of freshly distilled acryloyl chloride that has been dissolved in 2 ml of acetone are added dropwise at 0°, with stirring, to a solution of 300 mg of 5-aminofluorescein in 10 ml of acetone. After 2 hours, 5 ml of ether are added to the reaction mixture and the precipitate is filtered off with suction. After washing twice with ether, the yellowish-orange product is dried at room temperature under a high vacuum.

$^1$H-NMR (DMSO-$d_6$): 10.65 (s,1H); 7.75 (d,1H); 7.65 (d×d,1H); 7.5 (s broad,1H); 6.5 (s broad,2H); 6.2–6.45 (m,4H); 6.0 (d×d,1H); 5.57 (d×d,1H); IR (KBr): 2200–3650m (broad), 1693m, 1637m, 1591s $cm^{-1}$; MS: $M^+$ 402; absorption spectrum (EtOH): $\lambda_{max}$=445 nm, e=3 450; (EtOH+2% 0.1N NaOH): $\lambda_{max}$=501 nm, ε=71 600.

EXAMPLE A3

4-Acryloylamino-4',5'-dimethylfluorescein

A mixture of 24.8 g of 2-methylresorcinol and 21.8 g of 4-nitrophthalic acid anhydride is heated at 200° for 15 minutes. The cooled solid crude product is boiled up in ethanol, filtered while hot and filtered with suction. The crystalline red 4',5'-dimethyl-4(5)-nitrofluorescein mixture is processed further immediately.

8.7 g of sodium sulfide hydrate and 4.1 g of sodium hydrogen sulfide hydrate are added to a solution of 3.7 g of 4',5'-dimethyl-4(5)-nitrofluorescein in 150 ml of water and the mixture is heated at reflux for 2 hours. After cooling, 15 ml of glacial acetic acid are added and the resulting product is filtered off with suction. The crude product is heated in 300 ml of 2N hydrochloric acid and filtered while hot. The filtrate is cooled to room temperature and yields a crystalline precipitate which after being filtered off with suction is dissolved again in 350 ml of 0.5% sodium hydroxide solution. After the addition of 7 ml of glacial acetic acid the title compound precipitates and is filtered off with suction. The product is dissolved in 100 ml of diethyl ether and washed twice using 20 ml of water each time. The dried ether phase is concentrated and the residue is chromatographed on silica gel first with methylene chloride/methanol (85:15) and then with n-hexane/ethyl acetate (1:1) and ethyl acetate only as eluant, with the result that the mixture of the title compound is separated. 4-Amino-4',5'-dimethyl-fluorescein: $^1$H-NMR (DMSO-$d_6$): 9.9 (s broad,2H); 7.05 (s,1H); 7.0 (d×d,2H); 6.65 (d,2H); 6.5 (d,2H); 5.8 (s,2H); 2.35 (s,6H); IR (KBr): 2300–3650s (broad), 1755s, 1710s, 1625s, 1605s cm$^{-1}$; MS: M$^+$ 376; absorption spectrum (EtOH): $\lambda_{max}$=470 nm, e=6 500; (EtOH+2% 0.1N NaOH): $\lambda_{max}$=510 nm, $\epsilon$=88 000.

5-Amino-4',5'-dimethyl-fluorescein: $^1$H-NMR (DMSO-$d_6$): 10.05 (s,2H); 7.73 (d,1H); 6.9 (d×d,1H); 6.8 (d,2H); 6.7 (d,2H); 6.4 (s,2H); 6.25 (d,1H); 2.45 (s,6H); IR (KBr): 2100–3650m (broad), 1720m, 1700m, 1630s, 1600s cm$^{-1}$; MS: M$^+$ 376; absorption spectrum (EtOH): $\lambda_{max}$=471 nm, e=1 940; (EtOH+2% 0.1N NaOH): $\lambda_{max}$=510 nm, $\epsilon$=85 200.

4-Acryloylamino-4',5'-dimethylfluorescein

A solution of 36 mg of acryloyl chloride is added dropwise to a solution of 100 mg of 4-amino-4',5'-dimethylfluorescein in 4 ml of acetone. After being stirred at room temperature for 1.5 hours the reaction mixture is concentrated to 0.5 ml and the crystalline precipitate is triturated in ether. Filtration with suction and drying under a high vacuum yield the pure title compound in the form of yellow crystals that decompose from 200°.

$^1$H-NMR (DMSO-$d_6$): 10.85 (s,1H); 8.4 (d,1H); 7.9 (d×d, 1H); 7.2 (d×d,1H); 6.7 (d,2H); 6.55 (d,2H); 6.3 (d×d,1H); 5.8 (d×d,1H); 2.3 (s,6H); IR (KBr): 2200–3650m (broad), 1690m, 1630m, 1600s cm$^{-1}$; MS: M$^+$ 429; absorption spectrum (EtOH): $\lambda_{max}$=454 nm, e=12 300; (EtOH+2% 0.1N NaOH): $\lambda_{max}$=514 nm, $\epsilon$=77 700.

EXAMPLE A4

5-Acryloylamino-4',5'-dimethylfluorescein

In a manner analogous to that described in Example A4 the title compound is prepared in the form of yellow crystals from 100 mg of 5-amino-4',5'-dimethylfluorescein.

$^1$H-NMR (DMSO-$d_6$): 10.6 (s,1H); 7.8 (d,1H); 7.6 (d,1H); 7.5 (s broad,1H); 6.45 (d,2H); 6.3 (d,2H); 6.2 (d,1H); 5.7 (d,1H); 2.3 (s,6H); IR (KBr): 2000–3700m (broad), 1685m, 1635m, 1600s, 1585s cm$^{-1}$; MS: M$^+$ 429; absorption spectrum (EtOH): $\lambda_{max}$=454 nm, e=15 100; (EtOH+2% 0.1N NaOH): $\lambda_{max}$=514 nm, $\epsilon$=77 100.

EXAMPLE A5

4(5)-(2-(Methacryloyloxy)-ethylaminocarbonyl)-2-(11-hydroxy-3-oxo-3H-dibenzo[c,h]xanthen-7-yl)-benzoic acid 100 mg (0.17 mmol) of 4(5)-carboxy-2-(11-hydroxy-3-oxo-3H-dibenzo[c,h]xanthen-7-yl)-benzoic acid are added to a solution of 32 mg of 2-aminoethyl methacrylate hydrochloride and 41 mg of 1,8-bis(dimethylamino)naphthalene in 5 ml of tetrahydrofuran (THF). After 48 hours' stirring at room temperature a further 32 mg of 2-aminoethyl methacrylate hydrochloride and 41 mg of 1,8-bis(dimethylamino) naphthalene are added and the mixture is stirred for a further 48 hours. The reaction mixture is concentrated and the residue is chromatographed on silica gel first with methylene chloride/methanol (10:1) as eluant, the title compound being obtained in the form of purple crystals.

$^1$H-NMR ($CDCl_3$): 8.6 (d,4H); 8.45 (s,1H); 8.2 (d×d,1H); 8.1 (d×d,1H); 8.05 (d×d,1H); 7.5 (s,1H); 7.3–7.4 (m,8H); 7.2 (d,1H); 6.15 (d,1H); 5.95 (s,1H); 5.65 (m,1H); 5.45 (m,1H); 4.4 (t,2H); 4.2 (t,2H); 3.8 (t,2H); 3.6 (t,2H); 2.0 (s,3H); 1.8 (s,3H); IR (KBr): 2400–3650m (broad), 1750m, 1725s, 1650s cm$^{-1}$; MS: M+ 587.

EXAMPLE A6

In a manner analogous to that described in Examples A1 to A6 it is also possible to prepare the other compounds of formula I listed in Table 1.

TABLE 1

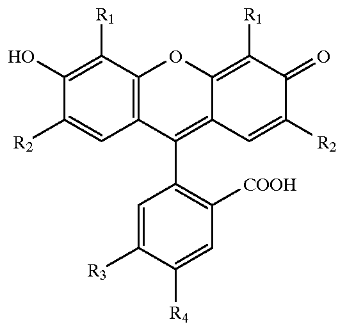

| No. | $R_1$ | $R_2$ | $R_3$ | $R_4$ |
|---|---|---|---|---|
| 1 | H | H | H | $NHCOC(CH_3)=CH_2$ |
| 2 | H | H | $NHCOC(CH_3)=CH_2$ | H |
| 3 | $CH_3$ | H | H | NHCO—HC=$CH_2$ |
| 4 | $CH_3$ | H | NHCO—HC=$CH_2$ | H |

TABLE 1-continued

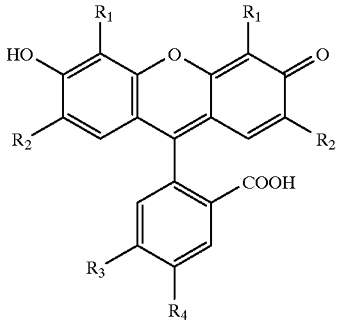

| No. | $R_1$ | $R_2$ | $R_3$ | $R_4$ |
|---|---|---|---|---|
| 5 | $CH_3$ | H | H | NHCO—$(CH_3)C{=}CH_2$ |
| 6 | $CH_3$ | H | NHCO—$(CH_3)C{=}CH_2$ | H |
| 7 | H | $CH_3$ | H | NHCO—$HC{=}CH_2$ |
| 8 | H | $CH_3$ | NHCO—$HC{=}CH_2$ | H |
| 9 | H | $CH_3$ | H | NHCO—$(CH_3)C{=}CH_2$ |
| 10 | H | $CH_3$ | NHCO—$(CH_3)C{=}CH_2$ | H |
| 11 | $CH_3$ | $CH_3$ | H | NHCO—$HC{=}CH_2$ |
| 12 | $CH_3$ | $CH_3$ | NHCO—$HC{=}CH_2$ | H |
| 13 | $CH_3$ | $CH_3$ | H | NHCO—$(CH_3)C{=}CH_2$ |
| 14 | $CH_3$ | $CH_3$ | NHCO—$(CH_3)C{=}CH_2$ | H |
| 15 | Cl | H | H | NHCO—$HC{=}CH_2$ |
| 16 | Cl | H | NHCO—$HC{=}CH_2$ | H |
| 17 | Cl | H | H | NHCO—$(CH_3)C{=}CH_2$ |
| 18 | Cl | H | NHCO—$(CH_3)C{=}CH_2$ | H |
| 19 | H | Cl | H | NHCO—$HC{=}CH_2$ |
| 20 | H | Cl | NHCO—$HC{=}CH_2$ | H |
| 21 | H | Cl | H | NHCO—$(CH_3)C{=}CH_2$ |
| 22 | H | Cl | NHCO—$(CH_3)C{=}CH_2$ | H |
| 23 | Cl | Cl | H | NHCO—$HC{=}CH_2$ |
| 24 | Cl | Cl | NHCO—$HC{=}CH_2$ | H |
| 25 | Cl | Cl | H | NHCO—$(CH_3)C{=}CH_2$ |
| 26 | Cl | Cl | NHCO—$(CH_3)C{=}CH_2$ | H |
| 27 | Br | H | H | NHCO—$HC{=}CH_2$ |
| 28 | Br | H | NHCO—$HC{=}CH_2$ | H |
| 29 | Br | H | H | NHCO—$(CH_3)C{=}CH_2$ |
| 30 | Br | H | NHCO—$(CH_3)C{=}CH_2$ | H |
| 31 | H | Br | H | NHCO—$HC{=}CH_2$ |
| 32 | H | Br | NHCO—$HC{=}CH_2$ | H |
| 33 | H | Br | H | NHCO—$(CH_3)C{=}CH_2$ |
| 34 | H | Br | NHCO—$(CH_3)C{=}CH_2$ | H |
| 35 | Br | Br | H | NHCO—$HC{=}CH_2$ |
| 36 | Br | Br | NHCO—$HC{=}CH_2$ | H |
| 37 | Br | Br | H | NHCO—$(CH_3)C{=}CH_2$ |
| 38 | Br | Br | NHCO—$(CH_3)C{=}CH_2$ | H |
| 39 | $CH_3O$ | H | H | NHCO—$HC{=}CH_2$ |
| 40 | $CH_3O$ | H | NHCO—$HC{=}CH_2$ | H |
| 41 | $CH_3O$ | H | H | NHCO—$(CH_3)C{=}CH_2$ |
| 42 | $CH_3O$ | H | NHCO—$(CH_3)C{=}CH_2$ | H |
| 43 | H | $CH_3O$ | H | NHCO—$HC{=}CH_2$ |
| 44 | H | $CH_3O$ | NHCO—$HC{=}CH_2$ | H |
| 45 | H | $CH_3O$ | H | NHCO—$(CH_3)C{=}CH_2$ |
| 46 | H | $CH_3O$ | NHCO—$(CH_3)C{=}CH_2$ | H |
| 47 | $CH_3OCO$ | H | H | NHCO—$HC{=}CH_2$ |
| 48 | $CH_3OCO$ | H | NHCO—$HC{=}CH_2$ | H |
| 49 | $CH_3OCO$ | H | H | NHCO—$(CH_3)C{=}CH_2$ |
| 50 | $CH_3OCO$ | H | NHCO—$(CH_3)C{=}CH_2$ | H |
| 51 | H | $CH_3OCO$ | H | NHCO—$HC{=}CH_2$ |
| 52 | H | $CH_3OCO$ | NHCO—$HC{=}CH_2$ | H |
| 53 | H | $CH_3OCO$ | H | NHCO—$(CH_3)C{=}CH_2$ |
| 54 | H | $CH_3OCO$ | NHCO—$(CH_3)C{=}CH_2$ | H |

EXAMPLE 7

Preperation of

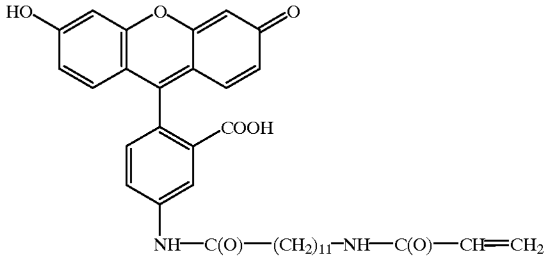

a) $H_3N^+$—$(CH_2)_{11}$—C(O)—O—$CH_3$ (a).

10 g 12-aminododecanoic acid are suspended in 200 ml of absolute methanole and 2.48 ml sulfuric acid (97%) are added. The clear solution is heated overnight under reflux. The pale yellow solution is evoporated to dryness and the obtained white crystals are washed with diethylether and dried subsequently. Yield: 15.4 g white powder, m. p. 73° C.

b) $CH_2$═CH—C(O)—NH—$(CH_2)_{11}$—C(O)—O—$CH_3$ (b).

3.25 (a) are disolved in 50 ml $CH_2Cl_2$ and 1 equivalent triethylamine is added. The reaction mixture is cooled to 5° C. and 2 equivalents acryloyl chloride dissolved in 10 ml $CH_2Cl_2$ are added dropwise. After 4 h reaction time at 0° C. the mixture is filtered and the filtrate evaporated to dryness. The crude product is dissolved in ethylacetate, washed with water, the organic phase is seperated and evoporated to dryness. Chromatographie on silica gel using ethylacetate as eluant yields 1.31 g (46%) white crystals, melting point: 65° C. $^1$H-NMR($CDCl_3$): 3.18 ppm ($OCH_3$).

c) $CH_2$═CH—C(O)—NH—$(CH_2)_{11}$—C(O)—OH (c).

Compound (b) is treated during 30 min with HCl (20%) at 60° C. in water. The reaction mixture is extracted after cooling with ethylacetate. The organic phase is wahed with water and brine and then dried. The solvent is evoporated yielding 80% crude product which is pure according NMR analysis. The product is directly used in the next process step.

d) Title compound

Compound (c) is dissolved in 15 ml terahydrofurane (THF) and 2.1 mmoles carbonyldiimidazole is added. After stirring (2 h) 2 mmoles 4-aminofluorescein dissolved in 60 ml THF are added and stirring is continued overnight. The solvent is evoporated and the residue chromatographied on silica gel. The product containing fractions are combined, dissolved in in NaOH and acidified with in HCl to preciti-pate the product. The product is isolated by centrifugation, washed twice with water and then centrifugated. Yield of title compound: 350 mg (30%); MS (FAB$^+$): 599.

EXAMPLE 8

Preperation of

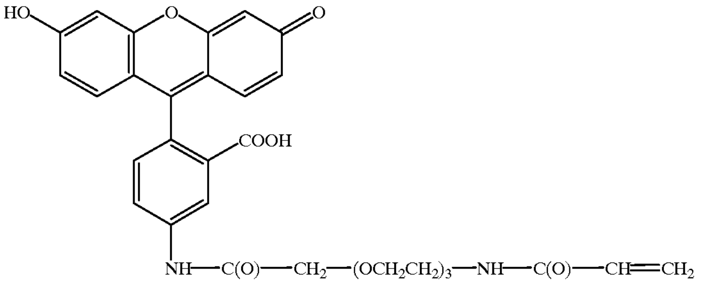

a) $N_3$—$(CH_2CH_2$—O—$)_3$H (a).

0.2 moles triethylene glycole chlorohydrine and 0.3 moles sodium azide are heated during 16 h at 110° C. The reaction mixture is cooled and filtered through a sintered glass funnel (P3). The filtrate is distilled and yields 86% product; boiling range 100 to 115° C./0.1 mm/Hg.

b) $N_3$—$(CH_2CH_2$—O—$)_3$—$CH_2$—C(O)—O—C$(CH_3)_3$ (b).

0.35 moles of (a) are slowly added to a suspension 0.385 moles sodium hydride in THF under cooling with an ice bath. After stirring for 1 h at room temperature 0.42 moles 2-bromo-t-butylacetate are dropwise added. Stirring is continued overnight. The solvent is evaporated, the dry residue taken up with diethylether, washed threetimes with water and once with brine. The solution is dried, the solvent is evaporated and the residue is distilled at 0.1 mm/Hg at 120–160° C. There are obtained 30% compound (b); $^1$H-NMR($CDCl_3$): 1.48 ppm (t-butyl), 4.05 ppm ($OCH_2$C(O)O).

c) $N_3$—$(CH_2CH_2$—O—$)_3$—$CH_2$—C(O)—OH (c).

6.9 mmoles compound (b) are dissolved in 30 ml dioxane, 100 mg Pd/C (5%) are added and the mixture is stirred for 6 h under a hydrogen atmosphere. After filtration and evaporation of the solvent there yields 99% of compound (c). $^1$H-NMR($CDCl_3$): 1.50 ppm (t-butyl).

d) $CH_2$=CH—C(O)—NH—($CH_2CH_2$—O—$)_3$—$CH_2$—C(O)—O—$C(CH_3)_3$ (d).

17.5 mmoles of compound (c) are dissolved in 50 ml $CH_2Cl_2$ and treated firstly with 21 mmoles triethylamine and secondly with 26.2 mmoles acryloyl chloride dissolved in 20 ml $CH_2Cl_2$ over a period of 40 minutes. The mixture is kept for 3 h at 0° C., then water is added, the organic phase is seperated, dried and the solvent evaporated. The crude product is used directly for the next reaction step.

e) $CH_2$=CH—C(O)—NH—($CH_2CH_2$—O—$)_3$—$CH_2$—C(O)—OH (e).

16.4 mmoles of compound (d) in 25 ml $CH_2Cl_2$ are treated during 5 h at room temperature with 25 ml trifluoroacetic acid. The solvent and acid are removed by distilliation yielding compound (e), $^1$H-NMR($CDCl_3$): 4.25 pp ($OCH_2$C(O)O), 5.75–5.85 and 6.3–6.4 (olefinic protons of acrylamide moiety).

f) Title compound 1.15 mmoles of compound (e) are dissolved in 5 ml THF and 1 equivalent carbonyldiimidazole is added at once. After 3 h stirring 1 mmole 4-aminofluorescein dissolved in 30 ml THF is added the resulting mixture is stirred for 48 hours. The sovent is dilled off and the residue is purified by chromatographie on silica gel. There yield 37% of the title compound; MS($FAB^-$): 589, MS($FAB^+$): 591.

B) Manufacture of planar sensors

EXAMPLE B1

Glass substrates (plates of 18 mm diameter) are first cleaned with 30% sodium hydroxide solution and then activated in 65% nitric acid. The activated plates are then silanised with methacrylic acid 3-trimethoxysilylpropyl ester. 150 μl of hydroxyethyl methacrylate, 5 mg of N,N-methylenebisacrylic acid amide, 2 mg of 4-acryloylaminofluorescein and 20 mg of ammonium peroxodisulfate are added to 4 ml of solution taken from a stock solution of 4 g of polyhydroxyethyl methacrylate in 60 ml of dimethylformamide. 50 μl of the resulting mixture are transferred by pipette to a plate lying on the head of a spin coater and the plate is spun for 30 seconds at a speed of 5000 revolutions per minute. For polymerisation the coated plates are then kept in an oven at 64° for 2 to 3 hours. Transparent substrates having a polymer layer of about 1 μm thickness are obtained. The polymer layer has good mechanical stability.

EXAMPLE B2

Glass substrates (plates of 18 mm diameter) are first cleaned with 30% sodium hydroxide solution and then activated in 65% nitric acid. The activated plates are then silanised with methacrylic acid 3-trimethoxysilylpropyl ester. 150 μl of hydroxyethyl methacrylate, 5 mg of N,N-methylenebisacrylic acid amide, 2 mg of 4-acryloylaminofluorescein and 10 mg of Irgacure 651® (photoinitiator, Ciba-Geigy AG) are added to 4 ml of solution taken from a stock solution of 4 g of polyhydroxyethyl methacrylate in 60 ml of dimethylformamide. 50 μl of the resulting mixture are transferred by pipette to a plate lying on the head of a spin coater and the plate is spun for 30 seconds at a speed of 5000 revolutions per minute. For polymerisation the coated plates are then irradiated with UV light (365 nm, 1300 μW/$cm^2$) for 10 to 20 minutes at room temperature. Transparent substrates having a polymer layer of about 1 μm thickness are obtained. The polymer layer has good mechanical stability.

EXAMPLE B3

In a manner analogous to that described in Examples B1 and B2 it is also possible to prepare the other membranes listed in Table 2 ("pseudo-penetration-networks").

TABLE 2

| polymer[1] | mg | sol | monomer[2] | μl | mg dye[3] | mg cross-linking agent[4] | mg initiator |
|---|---|---|---|---|---|---|---|
| PVP | 600 | DMF | VP | 300 | 4 | 10 | 40[5] |
| PVP | 600 | DMF | VP | 300 | 4 | 10 | 20[6] |
| PAA | 800 | $H_2O$ | AA | 150 | 2 | 5 | 20[5] |
| PHEMA | 270 | DMF | HEMA | 150 | 2 | 5 | 20[5] |
| PHEMA | 270 | DMF | HEMA | 150 | 2 | 5 | 10[6] |
| PHPMA | 1600 | DMF | HPMA | 300 | 4 | 10 | 40[5] |
| PHBA | 670 | DMF | HBA | 300 | 4 | 10 | 40[5] |

[1]PVP: polyvinylpyrrolidone, PAA: polyacrylamide, PHEMA: polyhydroxyethyl methacrylate, PHPMA: polyhydroxypropyl methacrylate, PHBA: polyhydroxybutyl acrylate
[2]VP: vinylpyrrolidone, AA: acrylamide, HEMA: hydroxyethyl methacrylate, HPMA: hydroxypropyl methacrylate, HBA: hydroxybutyl acrylate
[3]4-acryloylaminofluorescein
[4]N,N-methylenebisacrylic acid amide
[5]ammonium peroxodisulfate
[6]Irgacure 651
sol = solvent
DMF = dimethylformamide

EXAMPLE B4

N,N-Dimethylacrylamide and tert-butylacrylamide in the desired ratio are placed in an ampoule and dissolved in dimethyl sulfoxide so that a 30% solution is formed. After the addition and dissolution of α,α'-azoisobutyronitrile and 4-acryloylaminofluoresecein, the ampoule is repeatedly frozen, evacuated and gassed with nitrogen in order to remove oxygen. The polymerisation is carried out at 60° for 48 hours in a water bath. A transparent, highly viscous yellow mass is obtained which, with stirring and if necessary with heating, is dissolved in twice the amount of methanol (based on the amount of dimethyl sulfoxide used). The solution is added dropwise, with vigorous stirring, to 20 times the amount of distilled water or diethyl ether, the polymer formed being precipitated in the form of yellow flocks which rapidly agglutinate. The polymer is filtered, dried at 100° for 24 hours, then again dissolved in methanol and precipitated in water or diethyl ether. After removal of the mother liquor, the product is dried at 100° for 48 hours. The resulting brittle yellow solid is very hygroscopic. The copolymer composition is determined by FT-IR measurement, and the dye concentration is determined by UV spectroscopic measurement in the absorption maximum of the dye (pure dye: 442 nm, copolymerised dye: 454 nm). In a manner corresponding to that described it is possible to prepare the copolymer membranes listed in Table 3.

Glass substrates (plates of 18 mm diameter) are first cleaned with 30% sodium hydroxide solution and then activated in 65% nitric acid. The activated plates are then silanised with 3-aminopropyltrimethoxysilane. The silanised plates are allowed to react for 1 hour at room temperature in a solution of O-(N-succinimidyl)-6-(4'-azido-2'-nitrophenylamino)hexanoate in dimethylformamide/borax buffer (5:1). The polymer (5%) is dissolved in methanol at 20° to 25° and applied to the plate, which has been functionalised with azido groups, in the form of a thin film by means of spin coating at a speed of 500 revolutions per minute for 20 seconds, irradiated for 15 minutes and then dried under nitrogen for 12 hours at 60°. The layer thicknesses of the membranes are about 1 μm.

TABLE 3

| Examp. No. | DMAA[1] mol % | TBAA[2] mol % | AAF[3] wt % | yield % | content[4] mol % | inh. visc.[5] dl/g | conc.[6] wt. % |
|---|---|---|---|---|---|---|---|
| 1 | 20 | 80 | 1 | 86 | 82.80 | 1.287 | >1[7] |
| 2 | 30 | 70 | 1 | 70 | 72.13 | 1.261 | 0.7 |
| 3 | 40 | 60 | 1 | 70 | 64.13 | 1.163 | 0.6 |
| 4 | 45 | 55 | 1 | 56 | 59.77 | 1.545 | >1[7] |
| 5 | 50 | 50 | 1 | 66 | 55.53 | 1.220 | >1[7] |
| 6 | 55 | 45 | 1 | 60 | 52.25 | 1.573 | 0.6 |
| 7 | 60 | 40 | 1 | 48 | 34.98 | 1.692 | 0.5 |
| 8 | 70 | 30 | 1 | 68 | 27.65 | 1.538 | 1.2 |

[1]N,N-dimethylacrylamide
[2]tert-butylacrylamide
[3]4-acryloylaminofluorescein
[4]content of N,N-dimethylacrylamide
[5]0.5% by weight in THF at 25°
[6]concentration of 4-acryloylaminofluorescein, determined by UV spectroscopy
[7]estimated

EXAMPLE B5

35 mg (0.058 mmole) compound of example A7, 2,19 g of N,N-dimethylacrylamide, 2,81 g of t-butylacryl amide and 25 mg azobisisoburyronitrile are dissolved in 16.7 dimethylsulfoxide, placed in an ampoule and then frozen in liquid nitrogen. The ampoule is evacuated and then warmed to room temperature. Nitrogen is introduced and the mixture frozen by liquid nitrogen. The procedure is repeated three-times. The ampoule is kept for 5 d at 60° C. The yellow viscous product is dissolved in 25 ml hot methanol and the the product is precipitated by the addition of 1.5 l diethylether. The residue is again dissolved in 25 ml hot methanol and precipitated by the addition of 1.5 l diethylether. The orange-red product is dried at room temperature in high vacuum. Yield is 1.83 g (36.6%), glass transition temperature is 147.9° C., inherent viscosity (0.5% solution in methanol at 25° C.) is 2.06 dl/g. The concentration of the dyestuff in the polymer is 0.53 percent by weight.

EXAMPLE B6

Example B5 is repeated using the compound of example A8 instead of the compound of example A7. Yield is 4.05 g (81%), glass transition temperature is 150.8° C., inherent viscosity (0.5% solution in methanol at 25° C.) is 1.34 dl/g. The concentration of the dyestuff in the polymer is 0.44 percent by weight.

C) Application Examples

EXAMPLE C1

Two sensors are mounted one behind the other in two flow cells. The calibration solutions or sample solutions are metered and conveyed through the cells using pumps. The measuring arrangement is thermostatically controlled. The light of a halogen lamp (white light, excitation wavelength 480 nm) is conducted through an excitation filter and reflected on a dichroic mirror and focused onto the planar sensors using lenses. The fluorescent light (at 520 nm) emitted by the sensors is collected using the same lens system and guided by the dichroic mirror through an emission filter to a photodiode. The fluorescence of the sensors is recorded while being acted upon by the calibration or sample solutions. The measurement data obtained from the calibrations are evaluated with a partial least squares pattern recognition algorithm; the calculation method is then capable of determining the pH and the ionic strength from the measurement data obtained from the sample.

The following Tables give the effects of the different membrane compositions on the properties of the embedded fluorescent dyes. Since the variation in the ionic strength alters not only the $pK_a$ of the dye but also the pH of the measuring solution, and the latter in turn influences the maximum fluorescence intensity of the dye, in order to measure the pH using the described sensor system it is necessary for the ionic strength dependency both of the $pK_a$ of the dye and of the pH of the calibration buffer solution to be known. Tables 4 and 5 show examples of fluorescent dyes, their $pK_a$, and the ionic strength dependency of the $pK_a$ and of the pH with different sensor membrane compositions. Sensors from the following tables having different ionic strength dependencies can be selected for the pH determination.

TABLE 4

| polymer[1] | dye[2] | $pK_a$[3] | ionic strength dependency[4] | buffer curve displacement[5] |
|---|---|---|---|---|
| PVP | A | 6.3 | 0.02 | 0.02 |
| PAA | A | 6.4 | 0.13 | 0.10 |
| PHEMA | A | 7.0 | 0.28 | 0.25 |
| PHBA | A | 7.3 | 0.05 | 0.10 |
| PVP | B | 6.6 | 0.02 | 0.02 |
| PAA | B | 6.7 | 0.16 | 0.10 |
| PHEMA | B | 7.3 | 0.30 | 0.20 |
| PHPMA | B | 7.4 | 0.13 | 0.10 |

[1]for abbreviations see Table 2
[2]A: 4-acryloylaminofluorescein, B: 4-acryloylamino-4',5'-dimethylfluorescein
[3]at 0.1M ionic strength
[4]$pK_a$ displacement between the calibration curves in buffer solutions of 0.1M and 0.3M ionic strength
[5]pH displacement between the calibration curves in buffer solutions of 0.1M and 0.3M ionic strength

TABLE 5

| copolymer[1] wt. % tBuAA | dye[2] | $pK_a$[3] | ionic strength dependency[4] | buffer curve displacement[5] |
|---|---|---|---|---|
| 46.2 | A | 6.78 | 0.10 | −0.07 |
| 51.2 | A | 7.00 | 0.07 | −0.04 |
| 56.2 | A | 7.28 | 0.16 | +0.05 |
| 61.0 | A | 7.50 | 0.16 | +0.08 |
| 65.8 | A | >7.60 | — | ~0.10 |

[1]prepared from dimethylacrylamide and tert-butylacrylamide (tBuAA)
[2]A: 4-acryloylaminofluorescein (1 percent by weight)
[3]at 0.1M ionic strength
[4]$pK_a$ displacement between the calibration curves in buffer solutions of 0.1M and 0.3M ionic strength
[5]pH displacement between the calibration curves in buffer solutions of 0.1M and 0.3M ionic strength

TABLE 6

| polymer | $pK_a$[3] | ionic strength dependency[4] | buffer curve displacement[5] |
|---|---|---|---|
| Example B5 | 7,8 | 0.04 | −0.5 |

What is claimed is:

1. A method for the independent, reversible, optical determination of pH value and ionic strength of an aqueous sample, in which the method comprises contacting a first optical sensor and a second optical sensor with the aqueous sample, irradiating the optical sensors with exciting light to generate fluorescence, measuring the fluorescence generated, and calculating the pH value and the ionic strength from the measured fluorescence with reference to a standard calibration curve wherein the two optical sensors comprise, a) a carrier material, to which there is applied b) at least one water-insoluble layer of a polymer comprising at least one hydrophilic, substituted olefin monomer (A), wherein the first and second optical sensors have different polymers in layer b, and c) a proton-sensitive fluorescent dye which is bonded directly or via a bridge group to the spine of the polymer of layer b) or which is incorporated in the polymer of layer b).

2. A method according to claim 1 wherein the carrier material of the optical sensors is transparent and is a glass or transparent polymer.

3. A method according to claim 1 wherein the carrier material is planar.

4. A method according to claim 1 wherein the polymers in layer b) comprise at least 20 mol % of monomer (A), based on the polymer.

5. A method according to claim 1 wherein the hydrophilic monomer (A) is an olefinic monomer corresponding to formula XX $$Z_x—CR{=}CR_2 \qquad (XX)$$

wherein each R independently of the others is hydrogen or a hydrophobic substituent, and $Z_x$ is a hydrophilic radical.

6. A method according to claim 5 wherein the hydrophobic substituents are selected from $C_1$–$C_{12}$alkyl, $C_1$–$C_{12}$alkoxy, $C_1$–$C_{12}$haloalkyl, phenyl, halophenyl, $C_1$–$C_4$alkylphenyl, $C_1$–$C_4$alkoxyphenyl, carboxylic acid ester groups having a total of from 2 to 20 carbon atoms, —CN, F and Cl.

7. A method according to claim 5 wherein the hophilic radicals are selected from —OH, —O—($C_2$–$C_{12}$alkylene)—OH, —C(O)—$NH_2$, —C(O)—NH—($C_2$–$C_{12}$alkylene)—OH, —C(O)—N—($C_2$–$C_{12}$alkylene)$_2$—OH, —C(O)—NH—$C_1$–$C_{12}$alkyl, —C(O)—N—($C_1$–$C_{12}$alkyl)$_2$, pyrrolidonyl and —C(O)—O—($C_2$–$C_{12}$alkylene)—OH.

8. A method according to claim 1 wherein the thickness of layer b) is from 0.01 to 50 $\mu$m.

9. A method according to claim 1 wherein the difference in the ionic strength dependency of the sensors is at least 0.1, measured as the $pK_a$ displacement between the calibration curves in buffer solutions of 0.1M and 0.3M ionic strength.

10. A method according to claim 1 wherein the polymers in layer b) are cross-linked.

11. A method according to claim 1 wherein the polymers in layer b) comprise at least 20 mol % of monomer (A) and, accordingly, at most 80 mol % of a hydrophobic comonomer (B), based on the polymer.

12. A method according to claim 1 wherein polymer b) comprises from 20 to 100 mol % of at least one structural unit of formula III (III)

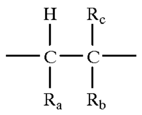

and from 80 to 0 mol % of at least one structural unit of formula IV (IV)

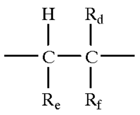

wherein $R_a$ is hydrogen, $C_1$–$C_6$alkyl or —$COOR_g$ and $R_g$ is hydrogen, $C_1$–$C_6$alkyl, $C_1$–$C_6$hydroxyalkyl or an alkali metal cation, for example $Na^{\oplus}$ or $K^{\oplus}$, $R_b$ is pyrrolidonyl, —OH, $C_2$–$C_6$hydroxyalkoxy, —$CONR_7R_8$ or —$COOR_9$, $R_7$ and $R_8$ are each independently of the other hydrogen, $C_1$–$C_6$alkyl or $C_2$–$C_6$hydroxyalkyl and $R_9$ is hydrogen or $C_1$–$C_6$hydroxyalkyl, $R_c$ is hydrogen or $C_1$–$C_6$alkyl, $R_d$ is hydrogen, $C_1$–$C_6$alkyl, F or Cl, $R_e$ is hydrogen or $C_1$–$C_6$alkyl, or $R_e$ and $R_f$ together are —CO—O—CO—, and $R_f$ is hydrogen, $C_1$–$C_6$alkyl, —CN, F or Cl.

13. A method according to claim 12 wherein the layer is composed of polymers having 100 mol % of structural units of formula III wherein $R_a$ is hydrogen, $R_c$ is hydrogen or methyl and $R_b$ is pyrrolidonyl, —$CONR_7R_8$ or —$COOR_9$, $R_7$ and $R_8$ are each independently of the other hydrogen, $C_1$–$C_6$alkyl or $C_2$–$C_6$hydroxyalkyl and $R_9$ is hydrogen or $C_2$–$C_6$hydroxyalkyl.

14. A method according to claim 1 wherein the layer of polymers comprises from 20 to 80 mol % of at least one structural unit of formula IIIa (IIIa)

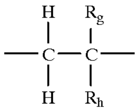

and from 80 to 20 mol % of at least one structural unit of formula IIIb (IIIb)

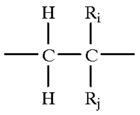

wherein $R_g$ and $R_i$ are each independently of the other hydrogen or methyl, preferably hydrogen;

$R_h$ is di($C_1$–$C_6$alkyl)amino, preferably di($C_1$–$C_4$alkyl)amino, and especially dimethylamino or diethylamino; and $R_j$ is amino, preferably mono($C_1$–$C_6$alkyl)amino and especially mono($C_1$–$C_6$alkyl)amino, for example tert-butylamino.

15. A method according to claim 1 wherein the hydrophilic polymers of layer b) are polymers comprising a polymerisate of at least one hydrophilic monomer (A) from the group of substituted olefins in which there is homogeneously distributed at least one carrier polymer comprising at least one hydrophilic monomer (A) from the group of substituted olefins that is identical to or different from the former.

16. A method according to claim 15 wherein the polymerisate is cross-linked and the carrier polymer is embedded in the polymer network.

17. A method according to claim 15 wherein the hydrophilic carrier polymer is a homo- or co-polymer of vinylpyrrolidone; of a hydroxyalkyl acrylate or methacrylate; of vinyl alcohol; of a vinylhydroxyalkyl ether; of an acrylamide or methacrylamide; or of a hydroxyalkyl acrylamide or methacrylamide.

18. A method according to claim 15 wherein the carrier polymer is composed of monomer (A), and monomer (A) is simultaneously used together with that carrier polymer for the preparation of the membrane.

19. A method according to claim 15 wherein the hydrophilic carrier polymer is polyvinylpyrrolidone, a poly ($C_2$–$C_6$hydroxyalkyl) acrylate or methacrylate, for example polyhydroxyethyl methacrylate, polyhydroxypropyl methacrylate, polyhydroxybutyl methacrylate, polyhydroxyhexyl methacrylate, polyhydroxyethyl acrylate, polyhydroxypropyl acrylate, polyhydroxybutyl acrylate or polyhydroxyhexyl acrylate, a polyacrylamide or polymethacrylamide, mono($C_1$–$C_6$alkyl)polyacrylamide or mono($C_1$–$C_6$alkyl)polymethacrylamide, di($C_1$–$C_6$alkyl) polyacrylamide or di($C_1$–$C_6$alkyl)polymethacrylamide.

20. A method according to claim 15 wherein the polymer of layer b) comprises at least one monomer (A) from the group: vinylpyrrolidone, 2-hydroxyethyl methacrylate, 3-hydroxypropyl methacrylate, 4-hydroxybutyl acrylate, 5-hydroxypentyl acrylate, 6-hydroxyhexyl acrylate, acrylamide, N,N-dimethylacrylamide and tert-butylacrylamide, or a polymer obtainable by polymerisation in solution of a monomer (A) from the group: vinylpyrrolidone, 2-hydroxyethyl methacrylate, 3-hydroxypropyl methacrylate, 4-hydroxybutyl acrylate, 5-hydroxypentyl acrylate, 6hydroxyhexyl acrylate and acrylamide, in the presence of a carrier polymer of a monomer (A) from the group consisting of vinylpyrrolidone, 2-hydroxyethyl methacrylate, 3-hydroxypropyl methacrylate, 4-hydroxybutyl acrylate and acrylamide.

21. A method according to claim 15 wherein the mixture ratio between monomer A and carrier polymer is from 5 to 95% by weight of carrier polymer, and from 95 to 5% by weight of monomer A, based on the total mixture of monomer and carrier polymer.

22. A method according to claim 1 wherein the polymers of layer b) are cross-linked with from 0.01 to 50 mol % of a cross-linking agent, based on the polymer.

23. A method according to claim 22 wherein the cross-linking agent is an acrylic or methacrylic acid ester or amide of a polyol or polyamine.

24. A method according to claim 1 wherein the fluorescent dye is present in an amount of from 0.01 to 10% by weight, based on the polymer.

25. A method according to claim 1 wherein the proton-sensitive fluorescent dye is selected from the group fluorescein, xanthenes and benzoxanthenes; acridines; acridones; pyrenes and coumarins, which are optionally covalently bonded directly or via a bridge group to the polymer.

26. A method according to claim 1 wherein the bridge group of the fluorescent dye is the group —$(CO)_s$—NH—($C_2$–$C_{12}$alkylene-O)$_r$—CO— or —$(CO)_s$—O—($C_2$–$Cl_2$alkylene-O)$_r$—CO— or —C(O)—NH—($CH_2CH_2$—O)$_{1\ bis\ 6}$—$CH_2C(O)$—NH—, with the $(CO)_s$ group or the NH group being bonded to the fluorescent dye and r and s each being 0 or 1.

27. A method according to claim 1 wherein the fluorescent dye is a dye of formula I, II or IIa (I)

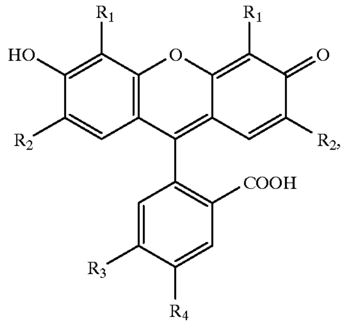

(II)

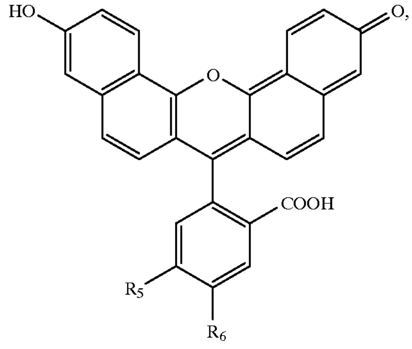

(IIa)

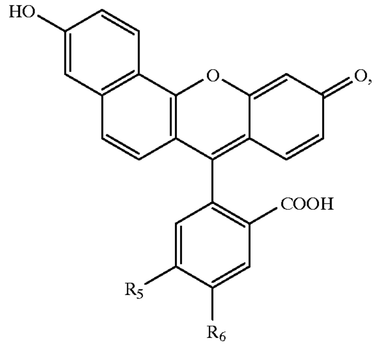

wherein $R_1$ and $R_2$ are each independently of the other hydrogen, $C_1$–$C_4$alkyl, $C_1$–$C_4$alkoxy, $C_1$–$C_4$alkoxycarbonyl, $C_1$–$C_4$-alkyl-$SO_2$ or halogen, and either $R_3$ is hydrogen and $R_4$ is —NH—CO—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_{1\ bis\ 6}$—$CH_2C(O)$—NH—, or $R_3$ is —NH—CO—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_{1\ bis\ 6}$—$CH_2C(O)$—NH— and $R_4$ is hydrogen; or wherein either $R_5$ is hydrogen and $R_6$ is —NH—C(O)—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_{1\ bis\ 6}$—$CH_2C(O)$—NH—, or $R_5$ is —NH—C(O)—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_{1\ bis\ 6}$—$CH_2C(O)$—NH—, and $R_6$ is hydrogen, in each case in free form or in salt form, or a $C_1$–$C_{20}$alkyl ester thereof.

* * * * *